(12) United States Patent
McGowan et al.

(10) Patent No.: US 9,637,425 B2
(45) Date of Patent: May 2, 2017

(54) NCN TRIANIONIC PINCER COMPLEXES AS CATALYSTS FOR OLEFIN POLYMERIZATION AND ISOMERIZATION

(71) Applicant: UNIVERSITY OF FLORIDA RESEARCH FOUNDATION, INC., Gainesville, FL (US)

(72) Inventors: Kevin P. McGowan, Gainesville, FL (US); Adam S. Veige, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 247 days.

(21) Appl. No.: 13/852,611

(22) Filed: Mar. 28, 2013

(65) Prior Publication Data

US 2013/0289326 A1    Oct. 31, 2013

Related U.S. Application Data

(63) Continuation-in-part of application No. PCT/US2011/052532, filed on Sep. 21, 2011.

(60) Provisional application No. 61/387,288, filed on Sep. 28, 2010.

(51) Int. Cl.
| | | |
|---|---|---|
| C07C 5/25 | (2006.01) |
| C07C 2/34 | (2006.01) |
| B01J 23/24 | (2006.01) |
| C07C 2/32 | (2006.01) |
| C07F 11/00 | (2006.01) |
| B01J 31/14 | (2006.01) |
| B01J 31/18 | (2006.01) |
| B01J 31/22 | (2006.01) |

(52) U.S. Cl.
CPC .......... *C07C 5/2587* (2013.01); *B01J 23/24* (2013.01); *B01J 31/143* (2013.01); *B01J 31/183* (2013.01); *B01J 31/1805* (2013.01); *B01J 31/2208* (2013.01); *C07C 2/32* (2013.01); *C07C 2/34* (2013.01); *C07C 5/2581* (2013.01); *C07F 11/00* (2013.01); *C07F 11/005* (2013.01); *B01J 2231/122* (2013.01); *B01J 2231/52* (2013.01); *B01J 2531/0244* (2013.01); *B01J 2531/62* (2013.01); *C07B 2200/09* (2013.01); *C07C 2531/22* (2013.01)

(58) Field of Classification Search
None
See application file for complete search history.

(56) References Cited

U.S. PATENT DOCUMENTS 8,846,950 B2 * 9/2014 Veige et al. .............. 548/402

FOREIGN PATENT DOCUMENTS

| WO | WO 00/78826 | * 12/2000 | ............. C08F 10/00 |
| WO | WO 2010-101993 | 9/2010 | |

OTHER PUBLICATIONS

McGowan et al. Organometallics, 2011, 30, 4949-4957.*
Smith et al. Organometallics, 2005, 24, 778-784.*
Ajjou, J.A.N. et al., "Kinetics and Mechanisms of Thermally Induced Alkane Eliminations from Silica-Supported Bis(alkyl)chromicum(IV) and -vanadium(IV) Complexes," *J. Am. Chem. Soc.*, 1998, pp. 13436-13443, vol. 120.
Ajjou, J.A.N. et al., "Synthesis and Characterization of Silica-Stabilized Chromium(IV) Alkylidene Complexes," *J. Am. Chem. Soc.*, 1998, pp. 415-416, vol. 120.
Bhandari, G. et al., "Paramagnetic (Benzyl)chromium Complexes as Homogeneous Ethylene Polymerization Catalysts," *Organometallics*, 1995, pp. 738-745, vol. 14.
Döhring, A. et al., Donor-Ligand-Substituted Cyclopentadienylchromium(III) Complexes: A New Class of Alkene Polymerization Catalyst. 1. Amino-Substituted Systems, *Organometallics*, 2000, pp. 388-402, vol. 19.
Emrich, R. et al., "The Role of Metallacycles in the Chromium-Catalyzed Trimerization of Ethylene," *Organometallics*, 1997, pp. 1511-1513, vol. 16, No. 8.
Esteruelas, M.A. et al., "Preparation, Structure, and Ethylene Polymerization Behavior of Bis(imino)pyridyl Chromium(III) Complexes," *Organometallics*, 2003, pp. 395-406, vol. 22.
Gibson, V.C. et al., "Chromium(III) complexes bearing N,N-chelate ligands as ethene polymerization catalysts," *Chem. Commun.*, 1998, pp. 1651-1652.
Gibson, V.C. et al., Synthesis, Structures and Ethylene Polymerisation Behavior of Low Valent β-Diketiminato Chromium Complexes, *Eur. J. Inorg. Chem.*, 2001, pp. 1895-1903.
Heintz, R.A. et al., "Structure and Reactivity of Trimethylsilylmethyl Complexes of Chromium, including the 13-Electron Alkyl Cp*Cr(CH$_2$SiMe$_3$)$_2$," *Organometallics*, 1998, pp. 5477-5485, vol. 17.
Jensen, V.R. et al., "Activity of Homogeneous Chromium(III)-Based Alkene Polymerization Catalysts: Lack of Importance of the Barrier to Ethylene Insertion," *Organometallics*, 2000, pp. 403-410, vol. 19.
Jones, D.J. et al., "Discovery of a new family of chromium ethylene polymerisation catalysts using high throughput screening methodology," *Chem. Commun.*, 2002, pp. 1038-1039.
Kestel-Jakob, A., et al. "Diimine Chromium Complexes as Catalyst Precursors for Homogeneous Ethylene Polymerization," *Jordan Journal of Chemistry*, 2007, pp. 219-233, vol. 2, No. 3.
Kim, W-K. et al., "[(Ph)$_2$nacnac]MCl$_2$(THF)$_2$ (M = Ti, V, Cr): A New Class of Homogeneous Olefin Polymerization Catalysts Featuring β-Diiminate Ligands," *Organometallics*, 1998, pp. 4541-4543, vol. 17.

(Continued)

*Primary Examiner* — Yun Qian
(74) *Attorney, Agent, or Firm* — Saliwanchik, Lloyd & Eisenschenk

(57) ABSTRACT

A catalyst comprising a NCN pincer ligand group VI complex is capable of being used as an olefin polymerization or isomerization catalyst that does not require an expensive cocatalyst. The complex has the NCN pincer ligand in a trianionic form with the group VI in the +3 oxidation state or the +4 oxidation state and complexed to an anionic hydrocarbon group, or the complex has the NCN pincer ligand in a dianionic form with the group VI in the +2 oxidation state. The complex is capable of initiating the polymerization of alkenes without an added activator. The presence of a water scavenger and activator or cocatalyst, such as triisobutylaluminum, increases the catalytic activity. The complex is capable of selectively isomerizing 1-alkenes to cis/trans 2-alkenes.

15 Claims, 8 Drawing Sheets

(56) References Cited

OTHER PUBLICATIONS

Köhn, R.D. et al., "Selective Trimerization of α-Olefins with Triazacyclohexane Complexes of Chromium as Catalysts," *Angew. Chem. Int. Ed.*, 2000, pp. 4337-4339, vol. 39, No. 3.
Köhn, R.D. et al., "Triazacyclohexane complexes of chromium as highly active homogeneous model systems for the Phillips catalyst," *Chem. Commun.*, 2000, pp. 1927-1928.
Leelasubcharoen, S. et al., "Unusual Transformations of a Bipyridine Ligand in Attempts to Trap a Terminal Chromium(III) Alkylidene," *Organometallics*, 2001, pp. 182-187, vol. 20.
Macadams, L.A. et al., "The $(Ph)_2$nacnac Ligand in Organochromium Chemistry," *Organometallics*, 2002, pp. 952-960, vol. 21.
Macadams, L.A. et al., "A Chromium Catalyst for the Polymerization of Ethylene as a Homogeneous Model for the Phillips Catalyst," *J. Am. Chem. Soc.*, 2005, pp. 1082-1083, vol. 127.
Richeson, D.S. et al., "Synthesis and Reaction Chemistry of a New Class of Paramagenic Chromium(III) Alkyls. Characterization of Complexes Formed by Insertion of Nitriles Into the Chromium-Carbon Bond," *Organometallics*, 1989, pp. 2570-2577, vol. 8.
Sarkar, S. et al., "NCN Trianionic Pincer Ligand Precursors: Synthesis of Bimetalllic, Chelating Diamide, and Pincer Group IV Complexes," *Inorg. Chem.*, 2010, pp. 5143-5156, vol. 49.
Small, B.L. et al, "New Chromium Complexes for Ethylene Oligomerization: Extended Use of Tridentate Ligands in Metal-Catalyzed Olefin Polymerization," *Macromolecules*, 2004, pp. 4375-4386, vol. 37.
Filippou, A.C. et al., "Unusually Stable Chromium(IV) Alkyls Bearing a Triamidoamine Ligand," *Organometallics*, 2003, pp. 3010-3012, vol. 22.
Koller, J. et al., "Synthesis and Characterization of $(2,6-^iPrNCN)HfCl_2^-$ and $(3,5-MeNCN)_2Hf^{2-}$ (where NCN = 2,6-bis[phenylazanidy]methylphenyl): New Trianionic Pincer Ligands," *Organometallics*, 2007, pp. 5438-5441, vol. 26.
Ohff, A. et al., "Isomerization of olefins by titanocene and zirconocene alkyene complexes," *Journal of Molecular Catalysis A: Chemical*, 1996, pp. 103-110, vol. 105.
Bergbreiter, D.E. et al., "Polymer-Bound Titanium Olefin Osomerization Catalysts," *Journal of Organometallic Chemistry*, 1981, pp. 47-53, vol. 28.
Jones, D.J. et al., Discovery and Optimization of New Chromium Catalysts for Ethylene Oligomerization and Polymerization Aided by High-Throughput Screening, *J. Am. Chem. Soc.*, 2005, pp. 11037-11046, vol. 127.

\* cited by examiner

NCN TRIANIONIC PINCER COMPLEXES AS CATALYSTS FOR OLEFIN POLYMERIZATION AND ISOMERIZATION

CROSS-REFERENCE TO RELATED APPLICATIONS

This application is a continuation-in-part of International Patent Application No. PCT/US2011/052532, filed Sep. 21, 2011, which claims the benefit of U.S. Provisional Application Ser. No. 61/387,288, filed Sep. 28, 2010, the disclosures of which are hereby incorporated by reference in their entirety, including any figures, tables, or drawings.

This invention was made with government support under Contract No. CHE-0748408 awarded by the National Science Foundation. The government has certain rights in the invention.

BACKGROUND OF INVENTION

The polymerization of ethylene, propylene and other α-olefins is a market in excess of 100 million tons and is growing at an annual rate of about 5 percent. The catalyst industry that supports the polyolefin industry has sales approaching a billion dollars in the US alone. The catalyst market is presently dominated by Ziegler/Natta catalysts with metallocene and other single-site catalysts growing as a proportion of the market. Most olefin polymerization catalysts are solid supported catalysts comprising titanium compounds in combination with cocatalysts, which are commonly organoaluminum. Other olefin polymerization catalysts include chromium catalysts, which can be chromium oxides on silica or silica alumina, the Phillips process, and supported chromacene, a metallocene based catalyst used in the Union Carbide process. Other common metallocene catalysts include mono- and bis-metallocene complexes of Ti, Zr or Hf, which are used commonly in combination with a cocatalyst, such as methylaluminoxane (MAO). Non-metallocene catalysts are complexes of various transition metals with other multidentate oxygen-based and nitrogen-based ligands and are typically combined with MAO or other cocatalyst.

The development of catalysts that do not require MAO or other expensive cocatalysts as an activator has proceeded slowly and few examples are found in the literature. For example, Bhandari et al., *Organometallics* 1995, 14, 738-45 discloses (benzyl)chromium (III) complexes that polymerize ethylene alone, or with a co-catalyst. Ajjou et al., *J. Am. Chem. Soc.* 1998, 120, 415-416 discloses a bis(neopentyl) chromium(IV) surface complex on amorphous silica that polymerizes ethylene and propylene. Heintz et al., *Organometallics* 1998, 17, 5477-5485 discloses Bis(trimethylsilylmethyl)($\eta^5$-pentamethylcyclopentadienyl) chromium(III) for the polymerization of ethylene. MacAdams et al. *J. Amer. Chem. Soc.*, 2005, 127, 1082-3 discloses [(2,6-Me$_2$Ph)$_2$ nacnacCr(OEt$_2$)CH$_2$SiMe$_3$]BARF where nacnac=2,4-pentane-N,N'-bis(aryl)ketiminato and BARF=B(3,5-(CF$_3$)$_2$ C$_6$H$_3$)$_4^-$ for the polymerization of ethylene. The absence of MAO presents possibilities for control of rates, stereochemistry, molecular weights, and molecular weight distributions that are easily achieved by the inclusion of a single catalytic species in a pure form. To this end, the development of single component catalysts or a catalyst that permits the use of an inexpensive activator or cocatalyst may result in improved polymers and/or polymerization processes for polyethylene and polypropylene.

Additionally, catalysts that polymerize ethylene have the potential for use as olefin isomerization catalysts. Isomerization of functionalized substrates can be catalyzed by transition metal complexes, and the isomerization of olefins is a very important type of reaction commercially. Specifically, 1-alkene isomerization is a key step in many industrial processes, particularly in petrochemical refining, and selective olefin isomerization under mild conditions is an important goal.

Transition metal catalyzed isomerization of terminal olefins to internal olefins has been accomplished by Ir, Ru, and Rh metal hydrides or by complexes that can be converted into metal hydrides in the presence of a proton source. Generally, these catalytic systems operate via a metal-hydride addition-elimination pathway with a 1,2-hydrogen migration, although Fe and Ru carbonyl and phosphine substituted carbonyl derivatives have been shown to isomerize 1-alkenes through a π-allyl hydride intermediate that results in a 1,3-hydrogen shift.

Isomerization from terminal to internal alkenes is thermodynamically favorable because of the higher stability of internal olefins, and equilibration of alkenes favors the formation of structures where, when possible, the double bond is far from the end of the carbon chain. Generally, known catalysts yield a thermodynamic equilibrium mixture of isomeric alkenes with little selectivity. High selectivity for the isomerization of 1-alkenes to 2-alkenes has been achieved when a conjugated diene product is formed, but only a few examples of highly selective olefin isomerization catalysts exist that do not depend on the formation of a conjugated product. For example, organotitaniums, Bergbreiter et al., *J. Organomet. Chem.* 1981, 208, 47, or titanocene and zirconocene alkyne derivatives, Ohff et al., *J Mol. Catal.* 1996, 105, 103, have been disclosed to selectively isomerize 1-alkenes to their corresponding 2-alkenes. Therefore, catalysts that can effectively isomerize 1-alkenes to internal alkenes with selectivity are desirable.

BRIEF SUMMARY

Embodiments of the invention are directed to NCN pincer ligand group VI metal complexes having an NCN pincer ligand in the dianionic or trianionic form and the group VI metal, in the +2 or +3 oxidation state or in the +4 oxidation state substituted with a hydrocarbon group, respectively. The group VI metal can be, for example, Cr, Mo or W and the hydrocarbon group can be a normal alkyl group or a phenyl group. The NCN pincer ligand in the triprotonated form can be:

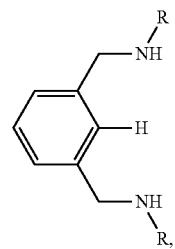

1

-continued

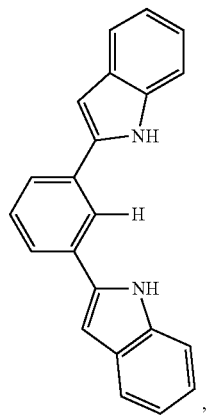

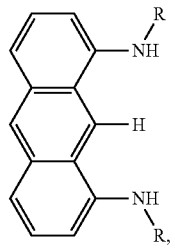

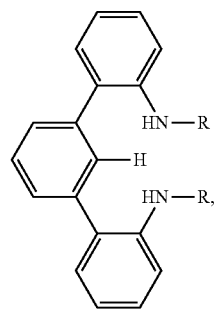

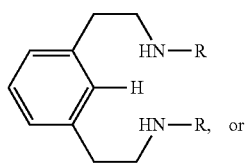

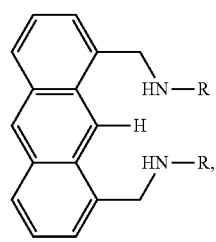

where R is 2,6-bis-(i-propyl)phenyl, 3,5-bis-(methyl)phenyl, 3,5-bis-(trifluoromethyl) phenyl, 3,5-bis-(i-propyl)phenyl, mesytyl, or tri-i-propylsilyl. The dianionic ligands display deprotonated amine groups and the trianionic ligands additionally display an anion resulting from the deprotonation of the central aromatic ring with all anions coordinated to the group VI metal ion as illustrated in the specific embodiments below. In a specific embodiment of the invention, the trianionic NCN pincer ligand complexed group VI metal alkyl is:

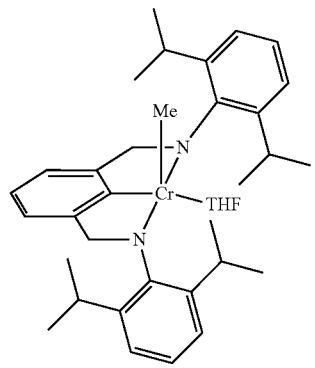

In another specific embodiment of the invention, the dianionic NCN pincer ligand complexed group VI metal is

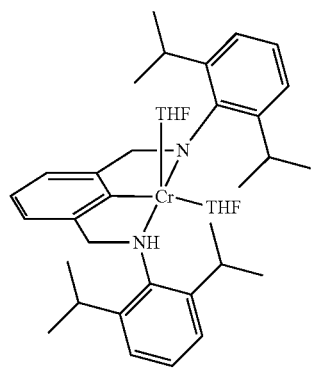

In another specific embodiment of the invention, the dianionic NCN pincer ligand complexed group VI metal is

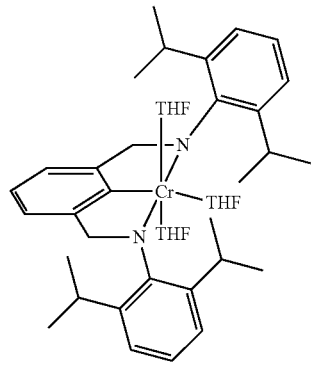

Another embodiment of the invention is directed to the preparation of a polyolefin by the above NCN pincer ligand group VI metal complexes by contacting a complex with an olefin monomer, where the complex initiates the polymerization of the olefin. The olefin can be ethylene, propylene, or butadiene.

In another embodiment of the invention, the isomerization of an α-olefin, a 1-alkene, to an internal olefin, primarily a 2-alkene, occurs upon contacting the above NCN pincer ligand group VI metal complexes with a 1-alkene of four or more carbon atoms.

DETAILED DISCLOSURE

Figure 1:
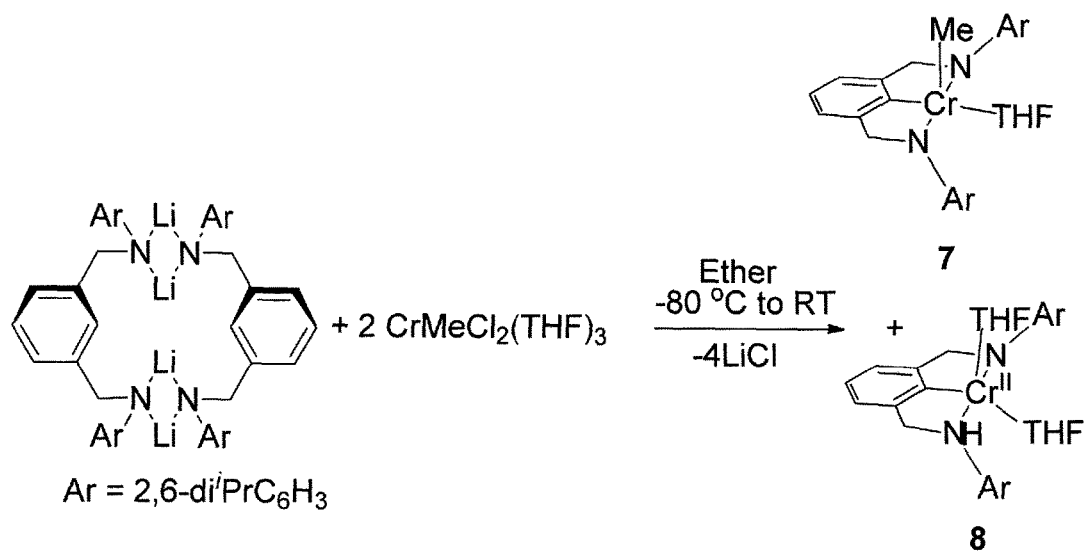
FIG. 1 is a reaction scheme for the preparation of 7 and 8 according to embodiments of the invention.

Embodiments of the invention are directed to trianionic NCN pincer ligated group IV or group VI metal hydrocarbon complexes or dianionic NCN pincer ligand derived group IV or group VI metal complexes of the generalized structures:

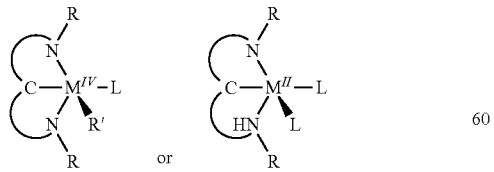

where M(IV) is a group VI metal (Cr, Mo, or W) or a group IV metal (Ti, Zr, or Hf), R' is an alkyl group or phenyl group, where the alkyl group can be methyl, ethyl, propyl, butyl, pentyl, or higher normal alkyl group and the NCN ligand and metal ion form a pair of five-member rings or a pair of six-member rings in the trianionic complexes or a single eight-member ring or ten-member ring in the dianionic complexes.

The triprotonated NCN pincer ligands are:

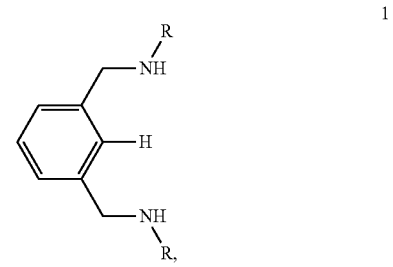

1

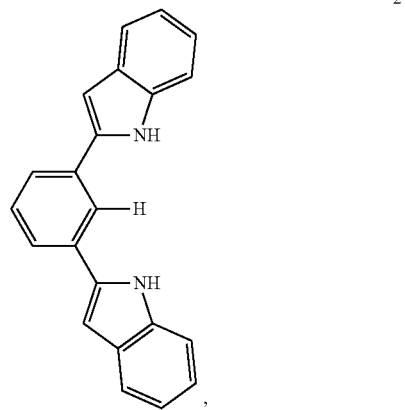

2

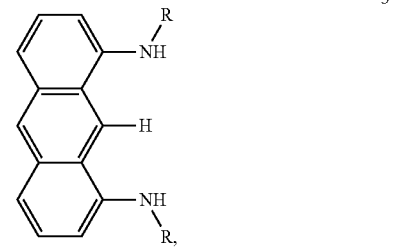

3

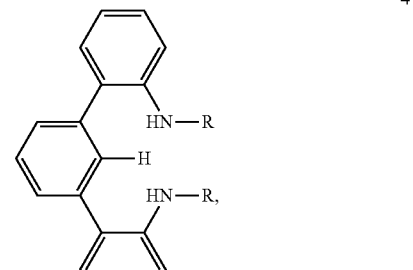

4

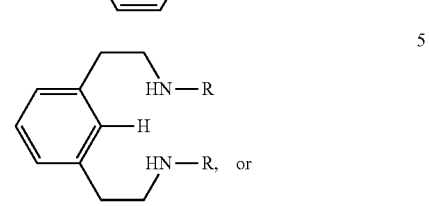

5

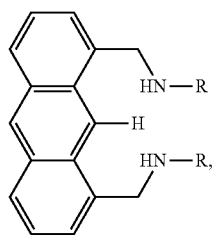

where R is 2,6-bis-(i-propyl)phenyl, 3,5-bis-(methyl)phenyl, 3,5-bis-(trifluoromethyl)phenyl, 3,5-bis-(i-propyl)phenyl, mesytyl, or tri-i-propylsilyl. All carbons positions not shown to have a H substituent can be independently substituted, for example, with alkyl groups such as methyl, ethyl, n-propyl, i-propyl, n-butyl, i-butyl t-butyl, or larger alkyl groups or any other substituent in a manner that does not inhibit formation of the metal complex, as can be appreciated by those skilled in the art. In the complexes according to embodiments of the invention, the trianionic forms of the ligands are:

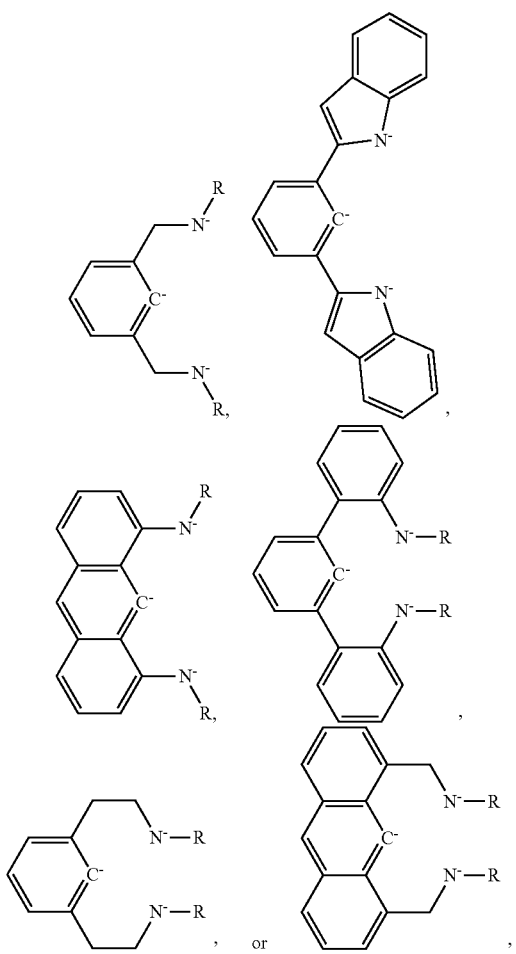

where R is defined as above and all carbons positions not shown with a negative charge or a hydrogen substituent can be independently substituted, for example, with alkyl groups such as methyl, ethyl, n-propyl, i-propyl, n-butyl, i-butyl t-butyl, or larger normal alkyl groups or any other substituent in a manner that does not inhibit formation of the metal complex. The dianionic form can be protonated on one of the nitrogen atoms or the central carbon atom.

Using an NCN pincer ligand, a Cr(IV) trianionic pincer ligand complex, for example, the complex:

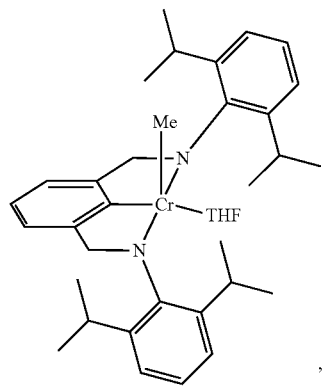

having the trianionic NCN pincer ligand from 1 where R is 2,6-bis-(i-propyl)phenyl, can be prepared and isolated. In like manner to the Cr complex having two five-member rings from 1, complexes from 2, and 3 can be formed. Furthermore, in like manner, Cr complexes having six-membered rings can be formed starting with 4, 5, and 6. Depending upon the NCN pincer ligand and the substituents on the ligand, the complex can be soluble, for example, in an aliphatic or aromatic hydrocarbon, an ether, or another organic solvents.

In another embodiment of the invention, a Cr(II) dianionic pincer ligand complex, for example the complex:

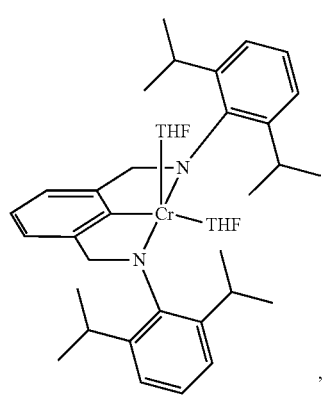

having the dianionic NCN pincer ligand from 1 where R is 2,6-bis-(i-propyl)phenyl, can be prepared and isolated. Depending upon the NCN pincer ligand and the substituents on the ligand, the complex is soluble, for example, in an aliphatic or aromatic hydrocarbon, an ether, or another organic solvent.

During studies on the preparation of Cr(II) dianionic pincer ligand complexes and Cr(IV) dianionic pincer ligand complex a new Cr(III) dianionic pincer ligand complex, according to an embodiment of the invention, incorporating the trianionic NCN pincer ligand from 1 where R is 2,6-bis-(i-propyl)phenyl, has been isolated. The Cr(III) complex is of the structure:

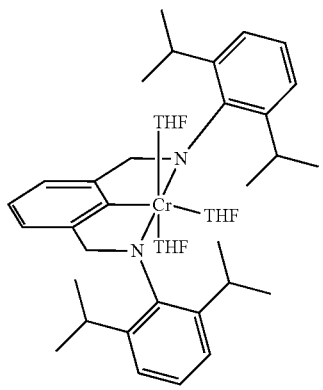

In another embodiment of the invention, the trianionic NCN pincer ligated metal alkyl complex and/or the dianionic NCN pincer ligand derived metal complex comprises a catalyst for the polymerization of alkenes. The catalysts do not require an expensive activator to initiate the polymerization. Instead, a compound, such as triisobutylaluminum (TIBA), is added, which removes spurious water and activates the system.

In another embodiment of the invention, the trianionic NCN pincer ligated metal alkyl complex and/or the dianionic NCN pincer ligand derived metal complex comprises an isomerization catalyst for the transformation of an a-olefin to an internal olefin. The a-olefin is any olefin containing at least one vinyl group having an adjacent methylene unit, for example, a 4 to 20 carbon olefin with one or more vinyl groups. The olefin can be straight chained or branched. The complex isomerizes a 1-alkene to cis/trans 2-alkene with a relatively high selectivity. Little conversion of the 2-alkene occurs to form a 3-alkene or more internal alkene.

Methods and Materials

General Considerations

Unless specified otherwise, all manipulations were performed under an inert atmosphere using standard Schlenk or glovebox techniques. Pentane, hexanes, toluene, diethyl ether, and tetrahydrofuran were dried using a GlassContour drying column. $C_6D_6$ and toluene-$d_3$ (Cambridge Isotopes) were dried over sodium-benzophenone ketyl, distilled or vacuum transferred and stored over 4 Å molecular sieves. Anhydrous $CrCl_2$, 1-hexene, 1-octene, and styrene oxide were purchased from Sigma-Aldrich and used as received. $CrMeCl_2(THF)_3$ and $\{[2,6\text{-}^iPrNCHN]Li_2\}_2^2$ were prepared according to a literature procedure. Triisobutylaluminum (25 wt. % in toluene) was purchased from Sigma-Aldrich and used as received. Ethylene (Matheson Purity 99.995%) was purchased from Matheson and used as received. Gas chromatography was performed on a Varian CP-3800 gas chromatograph using an intermediate polarity column. NMR spectra were obtained on Varian Gemini 300 MHz, Varian VXR 300 MHz, Varian Mercury 300 MHz, Varian Mercury Broad Band 300 MHz, Varian INOVA 500 MHz, or Varian INOVA2 500 MHz spectrometers. Chemical shifts are reported in δ (ppm). For $^1H$ and $^{13}C$ NMR spectra, the residual solvent peak was referenced as an internal reference. Variable temperature NMR experiments were performed in toluene-$d_8$. Infrared spectra were obtained on a Thermo scientific Nicolet 6700 FT-IR. Spectra of solids were measured as KBr discs. UV-visible spectra were recorded on a Cary 50 with scan software version 3.00(182). Gas chromatography was performed on a Varian CP-3800 gas chromatograph using an intermediate polarity column. EPR measurements were conducted using a Bruker Elexsys-500 Spectrometer at the X-band microwave frequency ~9.4 GHz at 20 K. The microwave frequency was measured with a built-in digital counter and the magnetic field was calibrated using 2,2-diphenyl-1-picrylhydrazyl (DPPH; g=2.0037). The temperature was controlled using an Oxford Instruments cryostat, to accuracy within ±0.1 K. Modulation amplitude and microwave power were optimized for high signal-to-noise ratio and narrow peaks. Mass spectrometry was performed at the in-house facility of the Department of Chemistry at the University of Florida. Accurate mass was determined by the electrospray ionization time-of-flight mass spectrometric (ESI-TOF) method in methanol. Combustion analyses were performed at Complete Analysis Laboratory Inc., Parsippany, N.J.

Synthesis of [2,6-$^i$PrNCN]CrMe(THF) (7)

Figure 2:
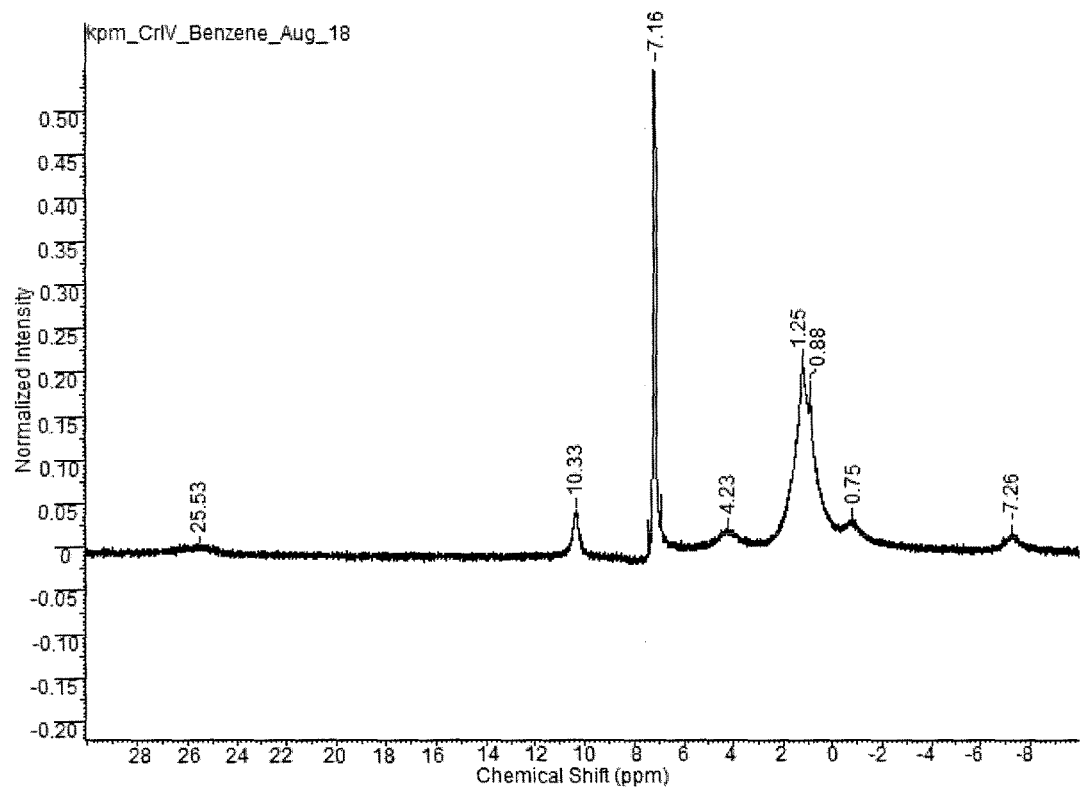
FIG. 2 is a $^1$H NMR spectrum of [2,6-$^i$PrNCN]CrMe (THF) (7) in benzene-$d_6$ according to an embodiment of the invention.
Figure 3:
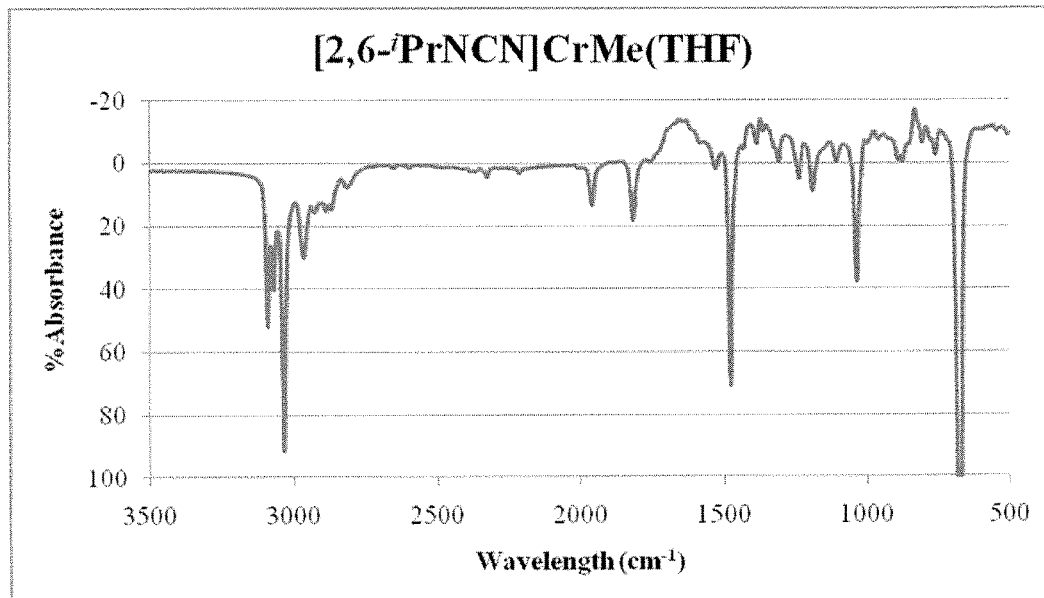
FIG. 3 shows an IR spectrum of [2,6-$^i$PrNCN]CrMe (THF) (7) according to an embodiment of the invention.
Figure 4:
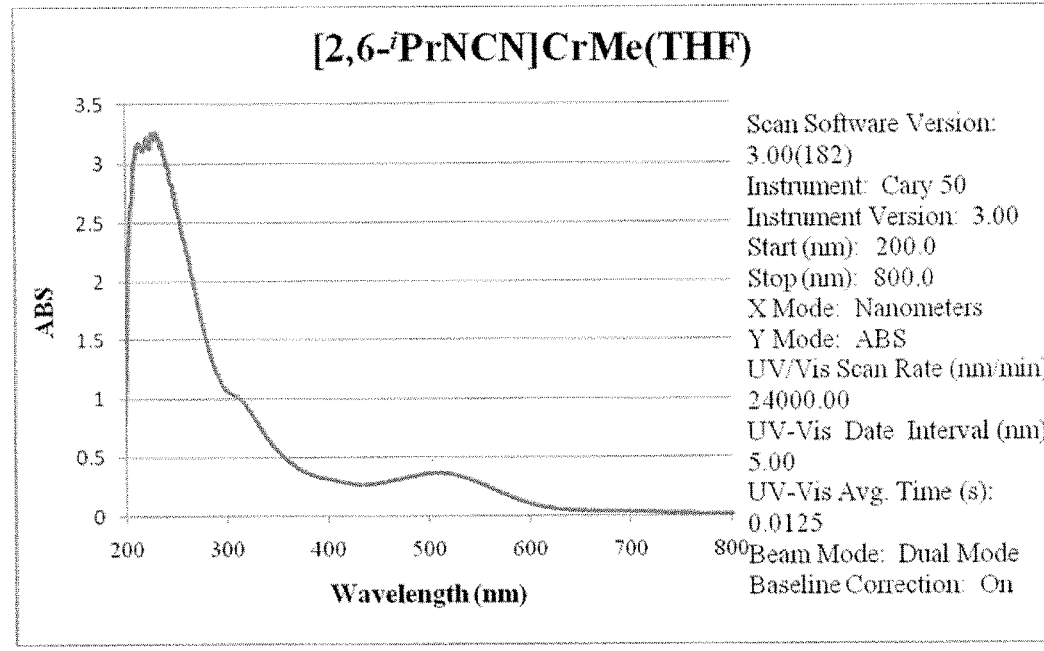
FIG. 4 shows an UV-Vis spectrum of [2,6-$^i$PrNCN]CrMe (THF) (7) in pentane according to an embodiment of the invention.

As indicated in FIG. 1, $CrMeCl_2(THF)_3$ (1.000 g, 2.84 mmol) was added to a solution of $\{[2,6\text{-}^iPrNCHN]Li_2\}_2$ (1.333 g, 1.42 mmol) in diethyl ether (50 mL) with stirring at −80° C. The reaction was warmed to ambient temperature and stirred for 1 hour. The solution was filtered and the filtrate was evaporated under vacuum to produce a dark solid. Pentane was added (50 mL) and the resulting slurry was filtered. Again, the filtrate was evaporated under vacuum to remove volatiles. The resulting purple-red oil was dissolved in minimal pentane and cooled to −35° C. to yield a purple precipitate. The product was isolated and purified by filtering the solution and washing with cold pentanes. X-ray quality single crystals were obtained by dissolving 2 in minimal diethyl ether and cooling to −35° C. Yield (185 mg, 10%). $^1H$ NMR (300 MHz, $C_6D_6$) δ (ppm): 25.53 (bs, $v_{1/2}$=360 Hz), 10.33 (bs, $v_{1/2}$=90 Hz), 4.23 (bs, $v_{1/2}$=300 Hz), −0.75 (bs, $v_{1/2}$=300 Hz), −7.23 (bs, $v_{1/2}$=165 Hz), as shown in FIG. 2, $\mu_{eff}$=2.68$\mu_B$. Anal. Calcd. for $C_{37}H_{52}CrN_2O$: C, 74.96; H, 8.84; N, 4.73. Found: C, 74.92; H, 8.96; N, 4.72. An IR spectrum is shown in FIG. 3 and an UV-Visible is shown in FIG. 4. X-ray quality single crystals were obtained by dissolving 7 in minimal diethyl ether and cooling to −35° C.

X-Ray Analysis of 7

Data were collected at 100 K on a Bruker DUO system equipped with an APEX II area detector and a graphite monochromator utilizing MoK$_\alpha$ radiation (λ=0.71073 Å). Cell parameters were refined using up to 9999 reflections. A hemisphere of data was collected using the co-scan method (0.5° frame width). Absorption corrections by integration were applied based on measured indexed crystal faces.

Figure 5:
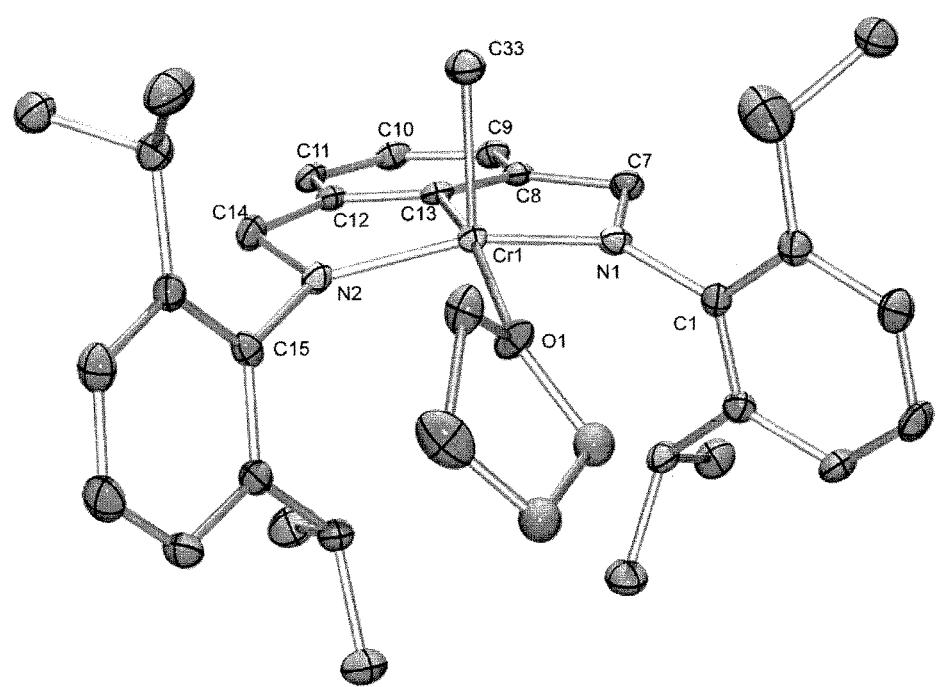
FIG. 5 is the molecular structure of [2,6-$^i$PrNCN]CrMe (THF) (7) according to an embodiment of the invention as determined by X-ray crystallography shown with ellipsoid presented at the 50% probability level and hydrogens removed for clarity.

The structure was solved by the Direct Methods in SHELXTL6, and refined using full-matrix least squares. The non-H atoms were treated anisotropically, whereas the hydrogen atoms were calculated in ideal positions and were riding on their respective carbon atoms. A $CH_2CH_2$ group of the coordinated THF ligand is disordered and refined in two parts with their site occupation factors dependently refined. A total of 366 parameters were refined in the final cycle of refinement using 5016 reflections with I>2σ(I) to yield $R_1$ and w$R_2$ of 4.40% and 10.49%, respectively. Refinement was done using $F^2$. The molecular structure is shown in FIG. 5. Tables 1 through 4, below, give the data determined by the X-ray Diffraction Analysis.

Synthesis of [2,6-$^i$PrNHCN]Cr(THF)$_2$ (8)

Figure 6:
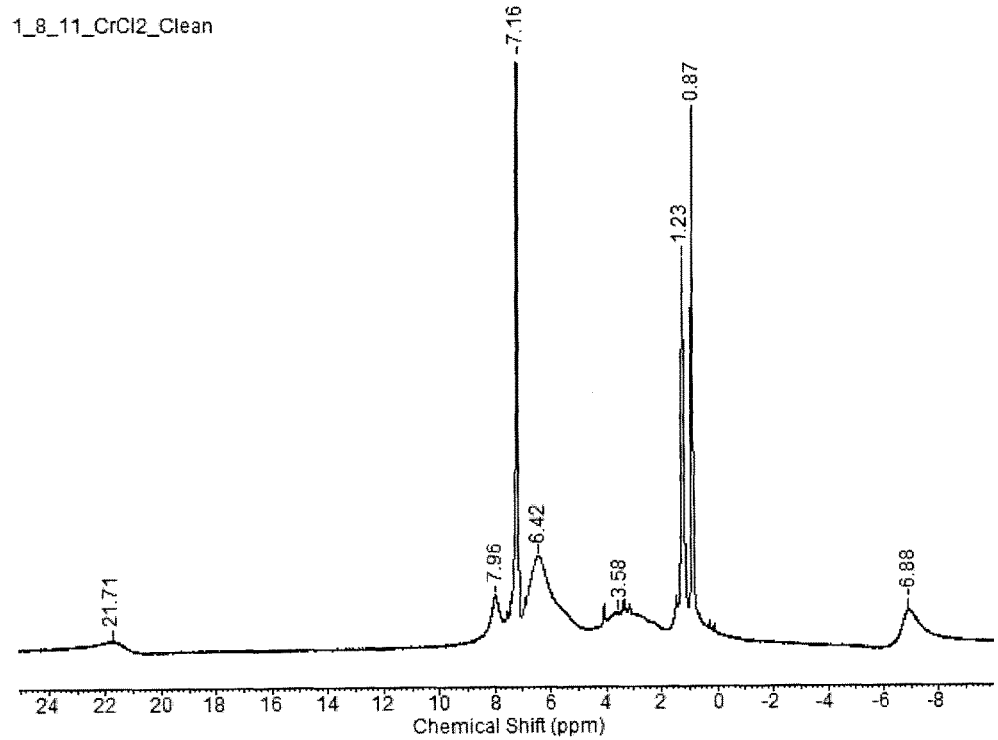
FIG. 6 is a $^1$H NMR spectrum of [2,6-$^i$PrNCN]Cr(THF)$_2$ (8) in benzene-$d_6$ according to an embodiment of the invention.
Figure 7:
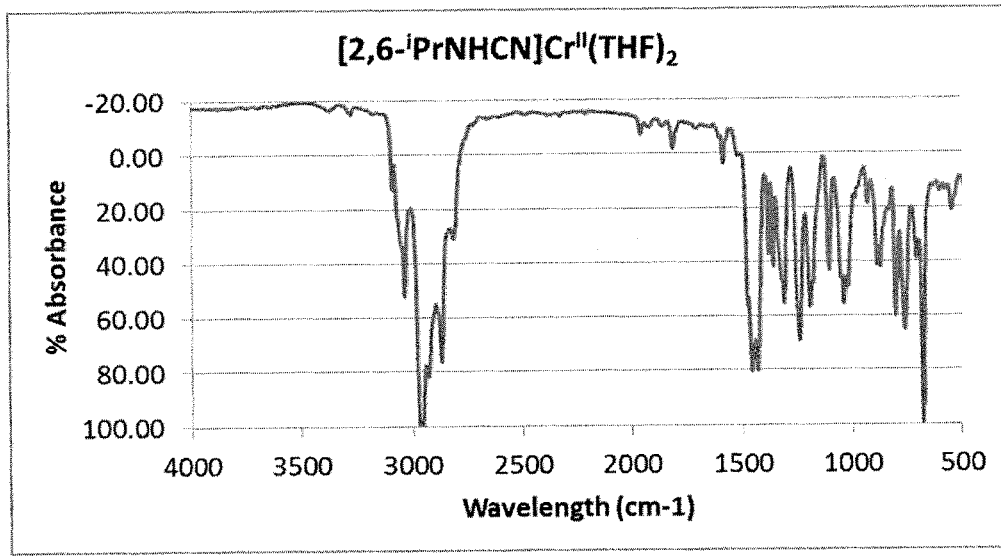
FIG. 7 shows an IR spectrum of [2,6-$^i$PrNCN]Cr(THF)$_2$ (8) according to an embodiment of the invention.
Figure 8:
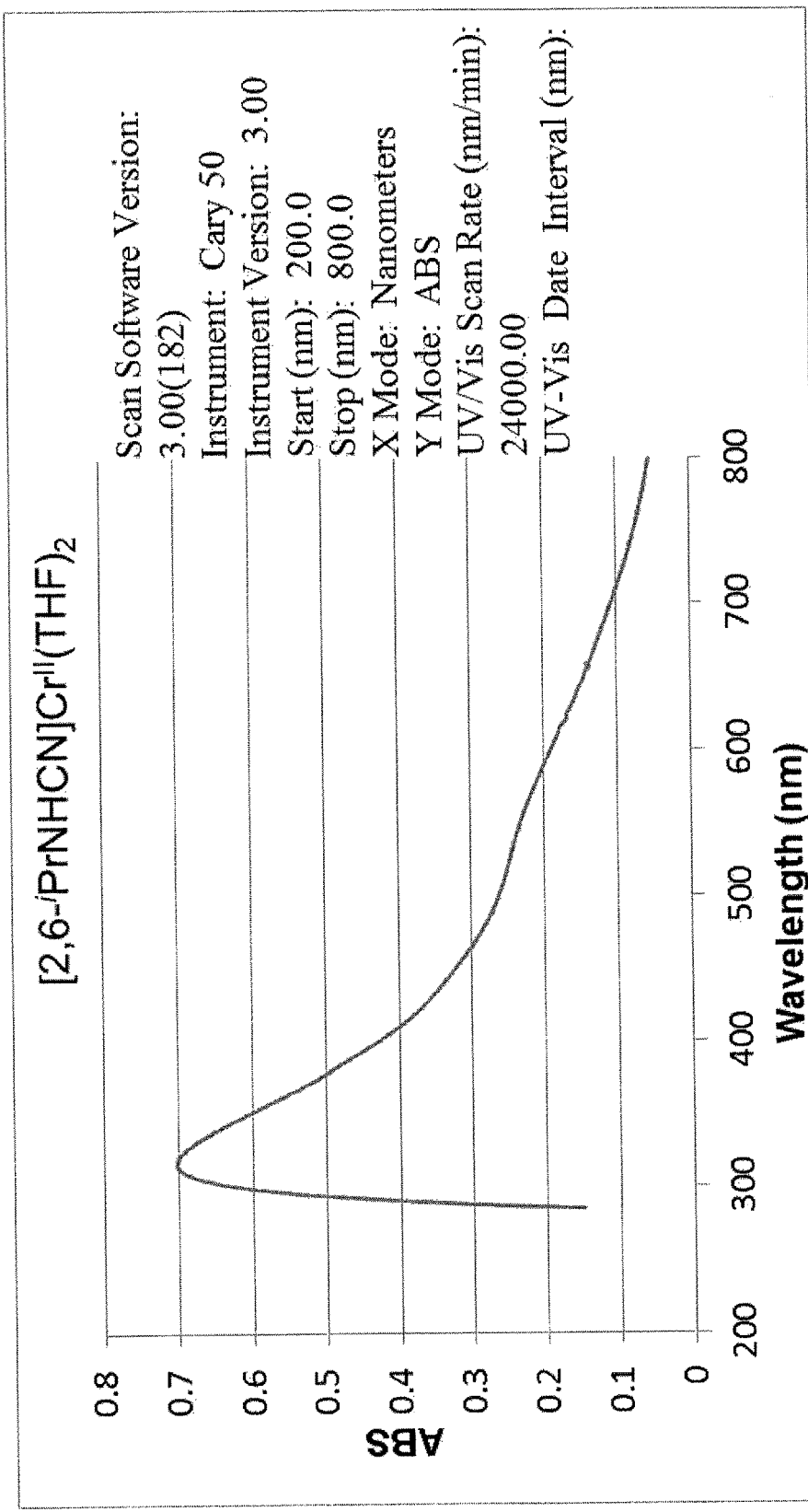
FIG. 8 shows an UV-Vis spectrum of [2,6-$^i$PrNCN]Cr (THF)$_2$ (8) in pentane according to an embodiment of the invention.

As indicated in FIG. 1, compound 8 was also isolated from the reaction mixture described above. The filtrate from the 7 precipitate was collected and the purple 7 precipitate was again dissolved in a minimal amount of pentane cooling to −35° C. and that precipitate was filtered and the second filtrate combined with the first filtrate. In like manner, a third filtrate was combined with the first and second filtrates that contained only 8 as product. Yield (220 mg, 12%). $^1$H NMR (300 MHz, $C_6D_6$) δ (ppm): 21.71 (bs, $v_{1/2}$=330 Hz), 7.96 (bs, $v_{1/2}$=150 Hz), 6.42 (bs, $v_{1/2}$=330 Hz), 3.54 (bs, $v_{1/2}$=685 Hz), −6.88 (bs, $v_{1/2}$=240 Hz), as shown in FIG. 6. $\mu_{eff}$=4.42 $\mu_B$. Anal. Calcd. for $C_{40}H_{58}CrN_2O_2$: C, 73.81; H, 8.98; N, 4.30. Found: C, 73.72; H, 8.85; N, 4.27. An IR spectrum is shown in FIG. 7 and an UV-Visible is shown in FIG. 8.

Alternatively, synthesis of 8 was carried out by adding anhydrous $CrCl_2$ (524 mg, 4.268 mmol) to a solution of $\{[2,6-^iPrNCHN]Li_2\}_2$ (2.00 g, 2.13 mmol) in THF (50 mL) with stirring at −80° C. The reaction mixture was warmed to ambient temperature, stirred for 1 hour, and vacuum applied to remove volatiles resulting in a solid. The solid was dissolved in pentane (50 mL), the solution was filtered, and the filtrate was evaporated under vacuum. The resulting purple-red oil was dissolved in a minimal quantity of ether and cooled to −35° C. to yield 8 as a purple precipitate. Yield (287 mg, 10%). $^1$H NMR (300 MHz, $C_6D_6$) δ (ppm): 21.71 (bs, $v_{1/2}$=330 Hz), 7.96 (bs, $v_{1/2}$=150 Hz), 6.42 (bs, $v_{1/2}$=330 Hz), 3.54 (bs, $v_{1/2}$=685 Hz), −6.88 (bs, $v_{1/2}$=240 Hz). $\mu_{eff}$=4.42 $\mu_B$. Anal. Calcd. for $C_{40}H_{58}CrN_2O_2$: C, 73.81; H, 8.98; N, 4.30. Found: C, 73.72; H, 8.85; N, 4.27.

Synthesis of $[2,6-^iPrNCN]Cr(THF)_3$ (9)

Figure 9:
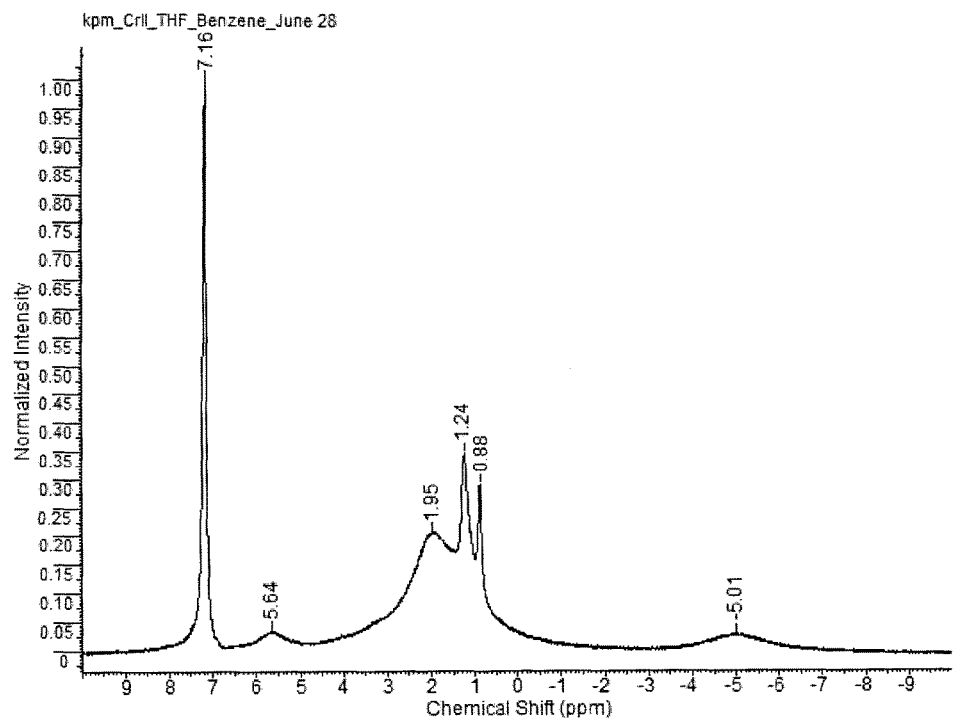
FIG. 9 is a $^1$H NMR spectrum of [2,6-$^i$PrNCN]Cr(THF)$_3$ (9) in benzene-$d_6$ according to an embodiment of the invention.
Figure 10:
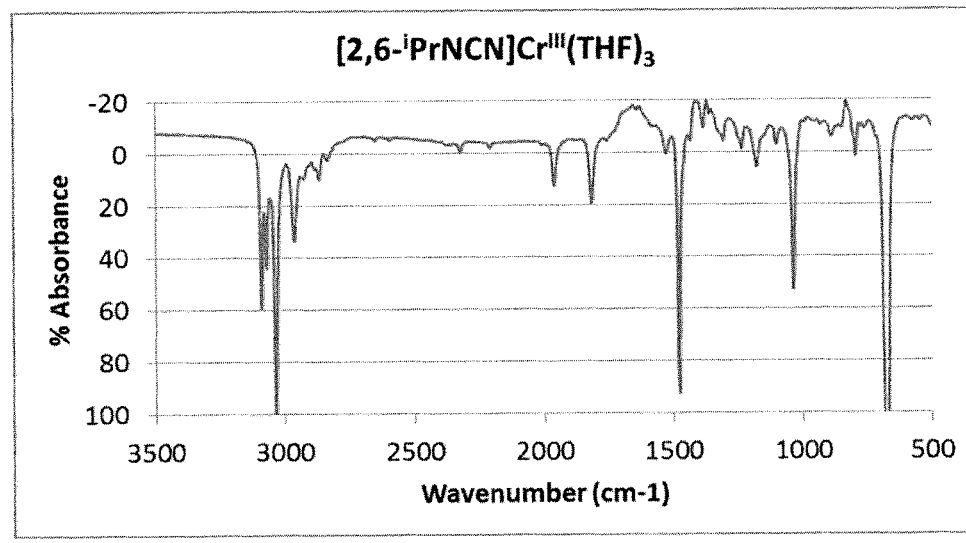
FIG. 10 shows an IR spectrum of [2,6-$^i$PrNCN]Cr(THF)$_3$ (9) according to an embodiment of the invention.
Figure 11:
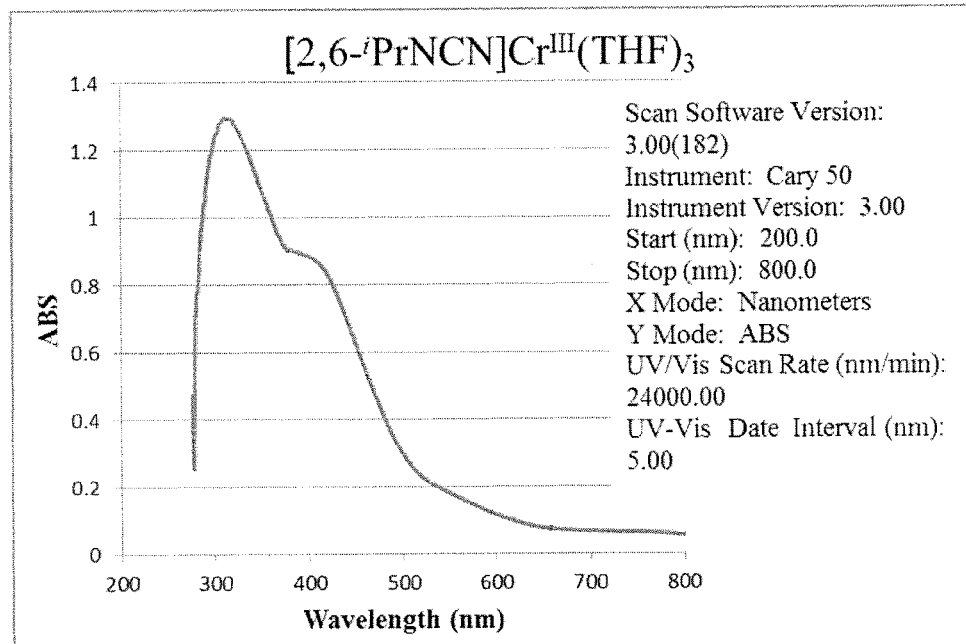
FIG. 11 shows an UV-Vis spectrum of [2,6-$^i$PrNCN]Cr (THF)$_3$ (9) in benzene according to an embodiment of the invention.

$CrMeCl_2(THF)_3$ (1.000 g, 2.84 mmol) was added to a solution of $\{[2,6-^iPrNCHN]Li_2\}_2$ (1.333 g, 1.42 mmol) in tetrahydrofuran (50 mL) with stirring at −80° C. The reaction was warmed to room temperature and stirred for 1 h and then all volatiles were removed under vacuum. Nonvolatile products were dissolved in pentane (50 mL) and filtered to collect an orange solid, which was evaporated under vacuum to remove all volatiles. The solid was dissolved in benzene (25 mL) and the solution was filtered, reduced under vacuum, and added to a stirring solution of pentane (50 mL) to precipitate 9 as a black crystalline solid. Yield (1.291 g, 63.0%). $^1$H NMR (300 MHz, $C_6D_6$) δ (ppm): 5.84 (bs, $v_{1/2}$=270 Hz), 1.95 (br s, $v_{1/2}$=420 Hz), −5.01 (bs, $v_{1/2}$=390 Hz), as shown in FIG. 9. $\mu_{eff}$=3.99 $\mu_B$. Anal. Calcd. for $C_{44}H_{62}CrN_2O_3$: C, 73.50; H, 8.69; N, 3.90. Found: C, 73.39; H, 8.51; N, 4.02. An IR spectrum is shown in FIG. 10 and an UV-Visible is shown in FIG. 11

TABLE 1

Crystal data, structure solution and refinement for 7.

| | |
|---|---|
| identification code | Mcg3 |
| empirical formula | $C_{37}H_{52}CrN_2O$ |
| formula weight | 592.81 |
| T (K) | 100 (2) |
| λ (Å) | 0.71073 |
| crystal system | Monoclinic |
| space group | C2/c |
| a (Å) | 34.092 (4) |
| b (Å) | 11.7102 (14) |
| c (Å) | 17.247 (2) |
| α (deg) | 90 |
| β (deg) | 104.138 (2) |
| γ (deg) | 90 |
| V (Å$^3$) | 6676.7 (14) |
| Z | 8 |
| $\rho_{calcd}$(Mg mm$^{-3}$) | 1.179 |
| crystal size (mm$^3$) | 0.38 × 0.19 × 0.03 |
| abs coeff (mm$^{-1}$) | 0.373 |
| F(000) | 2560 |
| θ range for data collection | 1.84 to 27.50 |
| limiting indices | −44 ≤ h ≤ 44, −15 ≤ k ≤ 15, −22 ≤ l ≤ 22 |
| no. of reflns collcd | 52816 |
| no. of ind reflns ($R_{int}$) | 7675 (0.0958) |
| Completeness to θ = 27.50° | 100.0% |
| absorption corr | Numerical |
| refinement method | Full-matrix least-squares on F$^2$ |
| data/restraints/parameters | 7675/0/366 |
| R1,$^a$ wR2$^b$ [I > 2σ(I)] | 0.0440, 0.1049 [5016] |
| R1,$^a$ wR2$^b$ (all data) | 0.0818, 0.1166 |
| GOF$^c$ on F$^2$ | 0.969 |
| largest diff. peak and hole | 0.542 and −0.610 e · Å$^{-3}$ |

$^a$R1 = Σ(||F$_o$| − |F$_c$||)/Σ|F$_o$|.
$^b$wR2 = (Σ(w(F$_o^2$ − F$_c^2$)$^2$)/Σ(w(F$_o^2$)$^2$))$^{1/2}$.
$^c$GOF = (Σ w(F$_o^2$ − F$_c^2$)$^2$/(n − p))$^{1/2}$ where n is the number of data and p is the number of parameters refined.

TABLE 2

Atomic coordinates (×10$^4$) and equivalent isotropic displacement parameters (Å$^2$ × 10$^3$) for 7. U(eq) is defined as one third of the trace of the orthogonalized Uij tensor.

| Atom | X | Y | Z | U(eq) |
|---|---|---|---|---|
| Cr1 | 6396(1) | 5490(1) | 5681(1) | 14(1) |
| O1 | 5882(1) | 5166(1) | 4664(1) | 19(1) |
| N1 | 6314(1) | 7096(2) | 5714(1) | 16(1) |
| N2 | 6707(1) | 4204(2) | 5550(1) | 16(1) |
| C1 | 6003(1) | 7794(2) | 5227(1) | 16(1) |
| C2 | 5676(1) | 8164(2) | 5525(1) | 17(1) |
| C3 | 5378(1) | 8841(2) | 5035(1) | 23(1) |
| C4 | 5403(1) | 9153(2) | 4278(1) | 26(1) |
| C5 | 6030(1) | 8100(2) | 4446(1) | 18(1) |
| C6 | 5724(1) | 8793(2) | 3992(1) | 23(1) |
| C7 | 6600(1) | 7775(2) | 6334(1) | 18(1) |
| C8 | 6971(1) | 7064(2) | 6631(1) | 15(1) |
| C9 | 7352(1) | 7415(2) | 7078(1) | 17(1) |
| C10 | 7664(1) | 6617(2) | 7250(1) | 18(1) |
| C11 | 7611(1) | 5498(2) | 6976(1) | 17(1) |
| C12 | 7231(1) | 5156(2) | 6532(1) | 15(1) |
| C13 | 6915(1) | 5932(2) | 6384(1) | 14(1) |
| C14 | 7108(1) | 4032(2) | 6128(1) | 16(1) |
| C15 | 6647(1) | 3370(2) | 4922(1) | 15(1) |
| C16 | 6403(1) | 2405(2) | 4942(1) | 18(1) |
| C17 | 6343(1) | 1626(2) | 4311(1) | 23(1) |
| C18 | 6525(1) | 1783(2) | 3686(1) | 24(1) |
| C19 | 6775(1) | 2710(2) | 3684(1) | 23(1) |
| C20 | 6845(1) | 3519(2) | 4298(1) | 17(1) |
| C21 | 5638(1) | 7883(2) | 6366(1) | 21(1) |
| C22 | 5232(1) | 7322(2) | 6377(2) | 31(1) |
| C23 | 5697(1) | 8948(2) | 6899(1) | 25(1) |
| C24 | 6379(1) | 7709(2) | 4109(1) | 21(1) |
| C25 | 6289(1) | 7769(2) | 3193(1) | 29(1) |
| C26 | 6773(1) | 8367(2) | 4462(2) | 30(1) |
| C27 | 6222(1) | 2170(2) | 5648(1) | 22(1) |
| C28 | 6368(1) | 1019(2) | 6034(1) | 27(1) |
| C29 | 5759(1) | 2198(2) | 5410(2) | 37(1) |
| C30 | 7126(1) | 4519(2) | 4279(1) | 19(1) |
| C31 | 7564(1) | 4120(2) | 4366(1) | 26(1) |
| C32 | 6987(1) | 5220(2) | 3513(1) | 26(1) |
| C33 | 6134(1) | 4948(1) | 6572(1) | 22(1) |
| C34 | 5467(1) | 5371(2) | 4693(1) | 22(1) |
| C35 | 5258(1) | 5793(2) | 3874(2) | 35(1) |
| C36 | 5470(2) | 5260(9) | 3345(4) | 24(1) |
| C37 | 5862(2) | 4716(7) | 3871(4) | 24(1) |
| C36' | 5476(2) | 4915(10) | 3329(4) | 24(1) |
| C37' | 5904(2) | 4942(8) | 3834(4) | 24(1) |

TABLE 3

Bond lengths (in Å) for 7.

| Bond | Length |
|---|---|
| Cr1—N2 | 1.8870(18) |
| Cr1—N1 | 1.9048(19) |
| Cr1—C13 | 1.953(2) |
| Cr1—C33 | 2.057(2) |
| Cr1—O1 | 2.1878(15) |
| O1—C34 | 1.448(3) |
| O1—C37 | 1.453(7) |
| O1—C37' | 1.476(7) |
| N1—C1 | 1.436(3) |
| N1—C7 | 1.488(3) |
| N2—C15 | 1.436(3) |
| N2—C14 | 1.496(3) |
| C1—C2 | 1.408(3) |
| C1—C5 | 1.418(3) |
| C2—C3 | 1.397(3) |
| C2—C21 | 1.523(3) |
| C3—C4 | 1.378(3) |
| C4—C6 | 1.372(3) |
| C5—C6 | 1.402(3) |
| C5—C24 | 1.517(3) |
| C7—C8 | 1.498(3) |
| C8—C13 | 1.392(3) |
| C8—C9 | 1.400(3) |
| C9—C10 | 1.394(3) |
| C10—C11 | 1.390(3) |
| C11—C12 | 1.394(3) |
| C12—C13 | 1.385(3) |
| C12—C14 | 1.500(3) |
| C15—C16 | 1.409(3) |
| C15—C20 | 1.413(3) |
| C16—C17 | 1.396(3) |
| C16—C27 | 1.517(3) |
| C17—C18 | 1.383(3) |
| C18—C19 | 1.380(3) |
| C19—C20 | 1.397(3) |
| C20—C30 | 1.518(3) |
| C21—C23 | 1.533(3) |
| C21—C22 | 1.535(3) |
| C24—C25 | 1.535(3) |
| C24—C26 | 1.538(3) |
| C27—C29 | 1.532(3) |
| C27—C28 | 1.532(3) |
| C30—C32 | 1.528(3) |
| C30—C31 | 1.537(3) |
| C34—C35 | 1.503(3) |
| C35—C36 | 1.438(8) |
| C35—C36' | 1.684(9) |
| C36—C37 | 1.555(10) |
| C36'—C37' | 1.504(10) |

TABLE 4

Bond angles (in deg) for 7

| Bonds | Angle |
|---|---|
| N2—Cr1—N1 | 152.00(8) |
| N2—Cr1—C13 | 80.56(8) |
| N1—Cr1—C13 | 80.64(8) |
| N2—Cr1—C33 | 101.71(9) |
| N1—Cr1—C33 | 100.82(9) |
| C13—Cr1—C33 | 96.34(9) |
| N2—Cr1—O1 | 97.41(7) |
| N1—Cr1—O1 | 95.75(7) |
| C13—Cr1—O1 | 165.78(8) |
| C33—Cr1—O1 | 97.85(8) |
| C34—O1—C37 | 105.7(3) |
| C34—O1—C37' | 110.1(3) |
| C37—O1—C37' | 12.3(4) |
| C34—O1—Cr1 | 122.80(12) |
| C37—O1—Cr1 | 131.5(3) |
| C37'—O1—Cr1 | 126.1(3) |
| C1—N1—C7 | 112.11(17) |
| C1—N1—Cr1 | 129.60(14) |
| C7—N1—Cr1 | 118.28(13) |
| C15—N2—C14 | 110.46(17) |
| C15—N2—Cr1 | 130.78(14) |
| C14—N2—Cr1 | 118.43(13) |
| C2—C1—C5 | 120.76(19) |
| C2—C1—N1 | 119.90(19) |
| C5—C1—N1 | 119.34(19) |
| C3—C2—C1 | 118.5(2) |
| C3—C2—C21 | 118.8(2) |
| C1—C2—C21 | 122.73(19) |
| C4—C3—C2 | 121.3(2) |
| C6—C4—C3 | 119.9(2) |
| C6—C5—C1 | 117.7(2) |
| C6—C5—C24 | 120.5(2) |
| C1—C5—C24 | 121.83(19) |
| C4—C6—C5 | 121.8(2) |
| N1—C7—C8 | 107.39(17) |
| C13—C8—C9 | 119.3(2) |
| C13—C8—C7 | 112.51(19) |
| C9—C8—C7 | 128.2(2) |
| C10—C9—C8 | 118.6(2) |
| C11—C10—C9 | 122.0(2) |
| C10—C11—C12 | 119.0(2) |
| C13—C12—C11 | 119.4(2) |
| C13—C12—C14 | 111.93(18) |
| C11—C12—C14 | 128.6(2) |
| C12—C13—C8 | 121.7(2) |
| C12—C13—Cr1 | 119.12(16) |
| C8—C13—Cr1 | 118.63(16) |
| N2—C14—C12 | 107.30(17) |
| C16—C15—C20 | 120.9(2) |
| C16—C15—N2 | 120.16(19) |
| C20—C15—N2 | 118.96(19) |
| C17—C16—C15 | 118.7(2) |
| C17—C16—C27 | 119.7(2) |
| C15—C16—C27 | 121.58(19) |
| C18—C17—C16 | 120.8(2) |
| C19—C18—C17 | 120.1(2) |
| C18—C19—C20 | 121.5(2) |
| C19—C20—C15 | 117.9(2) |
| C19—C20—C30 | 119.9(2) |
| C15—C20—C30 | 122.17(19) |
| C2—C21—C23 | 111.42(19) |
| C2—C21—C22 | 112.95(19) |
| C23—C21—C22 | 109.09(19) |
| C5—C24—C25 | 113.63(19) |
| C5—C24—C26 | 112.70(19) |
| C25—C24—C26 | 108.8(2) |
| C16—C27—C29 | 112.0(2) |
| C16—C27—C28 | 110.86(19) |
| C29—C27—C28 | 109.8(2) |
| C20—C30—C32 | 111.73(18) |
| C20—C30—C31 | 111.43(19) |
| C32—C30—C31 | 109.63(19) |
| O1—C34—C35 | 105.44(19) |
| C36—C35—C34 | 104.8(3) |
| C36—C35—C36' | 11.9(4) |
| C34—C35—C36' | 98.7(3) |
| C35—C36—C37 | 107.6(5) |
| O1—C37—C36 | 103.7(5) |
| C37'—C36'—C35 | 99.4(6) |
| O1—C37'—C36' | 107.1(5) |

Isomerization of 1-hexene using [2,6-$^i$PrNCN]CrMe(THF) (7)

A mixture of [2,6-$^i$PrNCN]CrMe(THF) (7) (10 mg, 0.017 mmol), 1-hexene (20.5 μL, 0.170 mmol), and benzene-$d_6$ (0.5 mL) was added to a sealable NMR tube under a nitrogen atmosphere. The reaction mixture was heated in a thermostated oil bath at 80° C. (±1° C.) for 72 hours. The reaction progress was monitored by $^1$H NMR spectroscopy at 48, 60, and 72 hours as indicated in Table 5, below. The reaction mixture was analyzed by $^1$H NMR spectroscopy to identify and quantify the organic products. In like manner, the isomerization of 1-octene using equivalent molar quantities, 26.5 µL of 1-octene, was investigated, with results given in Table 6, below.

Kinetic Measurements: A kinetic study was set up using the above method and the reaction progress was monitored by $^1$H NMR spectroscopy at 4, 8, 12, 16, 20, 24, 28, 32, and 36 hours. Conversion, as a percent of 1-hexene converted to 2-hexene, was determined by $^1$H NMR spectroscopy. This procedure was used to measure the isomerization of 1-octene.

Figure 12:
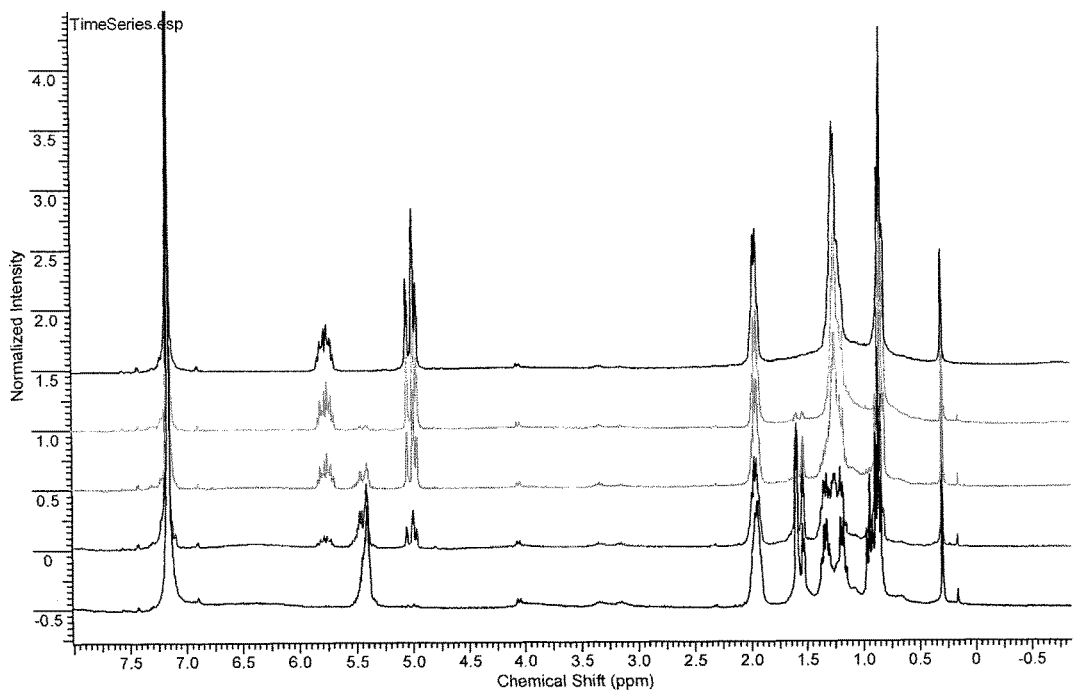
FIG. 12 is a composite of $^1$H NMR spectra in $d_6$-benzene of solutions of isomerizing 1-hexene solutions containing [2,6-$^i$PrNCN]CrMe(THF) (7) at 2 (top), 4, 8, 12, and 24 (bottom) hours according to an embodiment of the invention.
Figure 13:
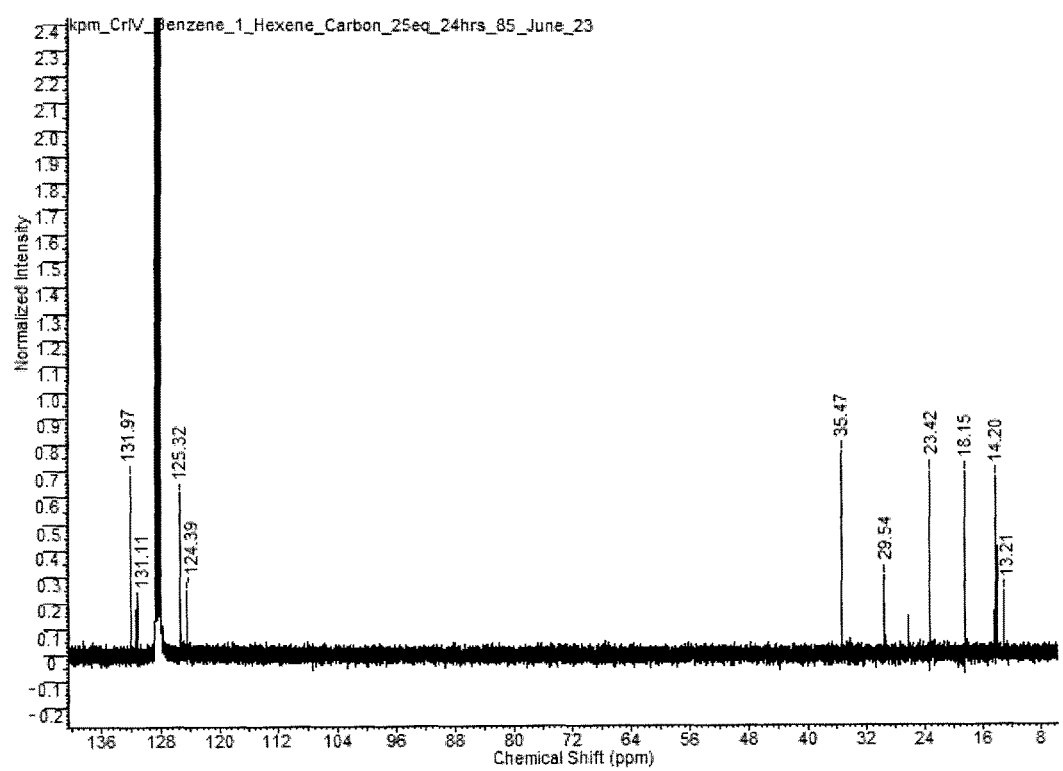
FIG. 13 is a $^{13}$C NMR spectrum obtained in $d_6$-benzene for the reaction products from 1-hexene in the presence of 7 after 24 hrs at 85° C., according to an embodiment of the invention.

Preheating (24 h, 85° C.): The sample setup was as above with the exception that alkene was not added initially. The reaction mixture in a sealable NMR tube was heated in a thermostated oil bath at 85° C. (+1° C.) for 24 hours. After heating, 1-hexene (52 µL, 0.422 mmol) was added to the NMR tube under a nitrogen atmosphere and returned to the oil bath. The reaction progress was monitored by $^1$H NMR spectroscopy at 2, 4, 8, 12, 16, 20, 24, 28, 32, 36 hours, as shown in FIG. 12 A $^{13}$C NMR spectrum of the reaction mixture in d$_6$-benzene after 24 hours is shown in FIG. 13. This procedure was used to measure the isomerization of 1-octene.

TABLE 5

Isomerization of 1-Hexene using 7 as Precatalyst

| Reaction Time (h) | Conversion (%)[a] | trans-2-hexene/ cis-2-hexene (%)[a] | trans-3-hexene/ cis-3-hexene (%)[a] |
|---|---|---|---|
| 48 | 90 (±5) | 95 (±2) | 5 (±2) |
| 60 | 95 (±1) | 92 (±2) | 8 (±2) |
| 72 | 96 (±0) | 87 (±3) | 13 (±3) |

[a]Percent conversion and product composition measured by $^1$H NMR (500 MHz).

TABLE 6

Isomerization of 1-Octene using 7 as Precatalyst

| Reaction Time (h) | Conversion (%)[a] | trans-2-octene/ cis-2-octene (%)[a] | trans-3-octene/ cis-3-octene (%)[a] |
|---|---|---|---|
| 48 | 90 (±3) | 88 (±2) | 12 (±2) |
| 60 | 95 (±2) | 86 (±3) | 14 (±3) |
| 72 | 97 (±0) | 82 (±3) | 18 (±3) |

[a]Percent conversion and product composition measured by $^1$H NMR (500 MHz).

Ambient Pressure Polymerization/Oligomerization using 7

To a sealed John-Young NMR tube under a nitrogen atmosphere, 7 (10 mg, 0.017 mmol) was added to benzene-d$_6$ (0.5 mL). The reaction mixture was evacuated, pressurized with 1 atm of ethylene, and then heated to 80° C. using a thermostatic bath. The reaction was allowed to run for 24 hr, after which MeOH was added to quench the reaction. The resulting polymer was isolated by filtration, rinsed, and thoroughly dried prior to weighing to yield 12 mg of polyethylene.

High Pressure Polymerization/Oligomerization using 7

Polymerization of Ethylene. Polymerization of ethylene to polyethylene (PE) was carried out for the catalyst loadings as indicated in Table 7, below. A 300 mL pressure reactor (Parr Instruments 4560 Series) was charged with 50 mL of toluene and triisobutylaluminum (TIBA), under nitrogen. The reactor was heated to an internal temperature of 75° C. Mechanical stirring was started, and the reactor was purged with ethylene. A solution of catalyst 7 in 1 mL of toluene was injected by syringe into the reactor, to give the catalyst loading indicated in Table 7. The reactor was pressurized to 20 bar with ethylene. Ethylene pressure was kept constant during the reaction. The reaction was carried out for 15 minutes, after which the reactor was vented and cooled. A known amount of cyclohexane was injected, a sample of the liquid was removed, and the sample was filtered for GC analysis. The polymeric material was collected by filtration, washed with acidified methanol (0.1 M), and dried under vacuum at 80° C. for 2 hours prior to weighing.

TABLE 7

Ethylene Polymerization by [2,6-$^i$PrNCN]CrMe(THF) (7)

| Catalyst Loading (µmol) | Ratio TIBA/Cr | Time (hours) | PE (grams) | Activity (kg/molCr/h) |
|---|---|---|---|---|
| 10 | 10 | 0.5 | 6.355 | 1,271 |
| 5 | 10 | 0.25 | 5.003 | 4,002 |
| 1 | 35 | 0.25 | 1.755 | 7,020 |

The polymerization of ethylene was carried out using various concentrations of the precatalyst and an activator or cocatalyst, to determine appropriate combinations to achieve high activities. Table 8, below, gives various formulations investigated with commonly used expensive cocatalysts for single site catalysis, tris(pentafluorophenyl)borane (FAB) and modified methylaluminoxane (MMAO), and with inexpensive TIBA. The higher activities were observed with TIBA, where the catalyst was employed at a low loading and a relatively low ratio of TIBA to 7 was used. As indicated in Table 8 and Table 7 activities as high as 7,020 kg/molCr/h were achieved at 1 µmol 7 and a TIBA/7 ratio of 35. Under similar conditions, the polymerization of ethylene was poor with MMAO and FAB as cocatalyst.

TABLE 8

Ethylene Polymerization by [2,6-$^i$PrNCN]CrMe(THF) (7)[a].

| Cocatalyst | 7 (µmol) | Cocatalyst/7 | Temp (° C.) | Mass PE (g) | Activity (kg/molCr/h) |
|---|---|---|---|---|---|
| none | 10[b] | N/A | 50 | 0 | 0 |
| none | 10[b] | N/A | 75 | 0 | 0 |
| MMAO | 10[b] | 10 | 50 | 0.090 | 18 |
| MMAO | 10[b] | 500 | 50 | 0.088 | 18 |
| FAB | 10[b] | 1 | 50 | trace | 0 |
| FAB | 10[b] | 10 | 50 | trace | 0 |
| TIBA | 5 | 10 | 25 | 0.473 | 378 |
| TIBA | 5 | 10 | 50 | 1.017 | 814 |
| TIBA | 5 | 10 | 75 | 5.003 | 4,002 |
| TIBA | 5 | 10 | 100 | 3.688 | 2,950 |
| TIBA | 5 | 1 | 75 | trace | 0 |
| TIBA | 5 | 2 | 75 | trace | 0 |
| TIBA | 5 | 5 | 75 | 0.126 | 101 |
| TIBA | 5 | 20 | 75 | 1.206 | 965 |
| TIBA | 5 | 50 | 75 | 0.632 | 506 |
| TIBA | 5 | 100 | 75 | 0.608 | 486 |
| TIBA | 1 | 10 | 75 | 0 | 0 |
| TIBA | 1 | 20 | 75 | 0.188 | 472 |
| TIBA | 1 | 30 | 75 | 1.002 | 4,008 |
| TIBA | 1 | 35 | 75 | 1.755 | 7,020 |
| TIBA | 1 | 40 | 75 | 1.592 | 6,368 |
| TIBA | 1 | 45 | 75 | 0.791 | 3,164 |
| TIBA | 1 | 50 | 75 | 0.615 | 2,460 |
| TIBA | 5[c] | 10 | 75 | 0.981 | 785 |

[a]Unless otherwise stated, reactions were performed in a 300 mL pressure reactor using toluene (50 mL) as solvent for 15 min at 20 bar of ethylene.
[b]t = 30 min.
[c]Pressure = 5 bar of ethylene.

All publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A catalyst, comprising a NCN pincer ligand group VI metal complex, wherein the NCN pincer ligand is in the dianionic form or trianionic form having the structures:

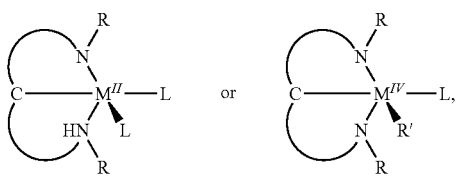

wherein the group VI metal is in the +2 oxidation state or +4 oxidation state where the NCN pincer ligand with N and C are nitrogen and carbon anion sites of the NCN pincer ligand and HN is a neutral site and metal ion form a pair of five-member rings or a pair of six-member rings in the complexes and where R is 2,6-bis-(i-propyl)phenyl, 3,5-bis-(methyl)phenyl, 3,5-bis-(trifluoromethyl) phenyl, 3,5-bis-(i-propyl)phenyl, mesytyl, or tri-i-propylsilyl and R' is a normal alkyl group or a phenyl group, and wherein the NCN pincer ligand in the triprotonated form is:

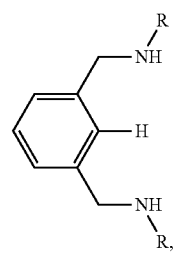

1

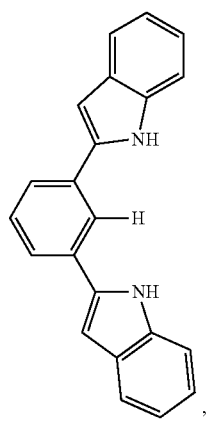

2

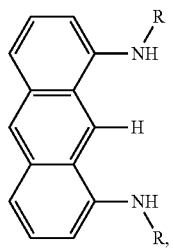

3

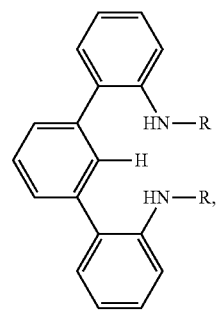

4

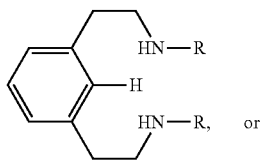

5

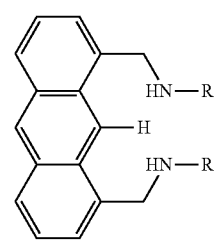

6 where R is 2,6-bis-(i-propyl)phenyl, 3,5-bis-(methyl)phenyl, 3,5-bis-(trifluoromethyl) phenyl, 3,5-bis-(i-propyl)phenyl, mesytyl, or tri-i-propylsilyl and where L is tetrahydrofuran (THF).

2. The catalyst of claim 1, wherein the group VI metal is Cr, Mo or W.

3. The catalyst of claim 1, wherein the NCN pincer ligand complexed group VI metal alkyl is

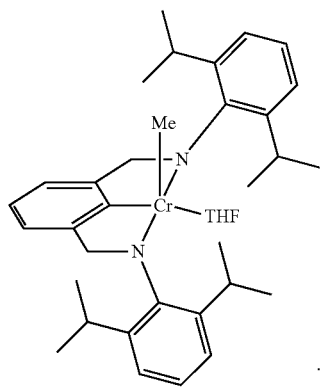

4. The catalyst of claim 1, wherein the NCN pincer ligand complexed group VI metal is

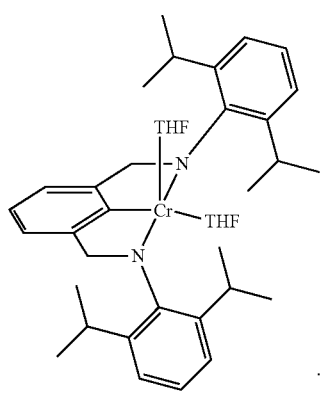

5. The catalyst of claim 1, wherein the trianionic NCN pincer ligand group VI metal alkyl complex is soluble in an organic solvent.

6. A method for the preparation of a polyolefin, comprising:
   providing a NCN pincer ligand group VI metal complex according to claim 1;
   providing one or more olefin monomers; and
   contacting the complex with the monomers, wherein the complex initiates the polymerization of the olefin.

7. The method of claim 6, further comprising providing triisobutylaluminum (TIBA).

8. The method of claim 6, wherein the NCN pincer ligand group VI metal complex has the structure:

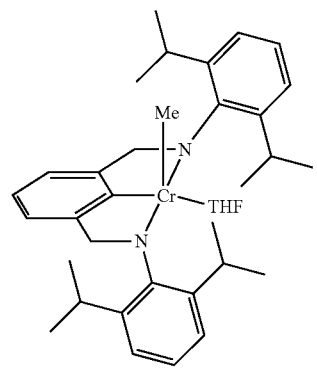

9. The method of claim 6, wherein the NCN pincer ligand group VI metal complex has the structure:

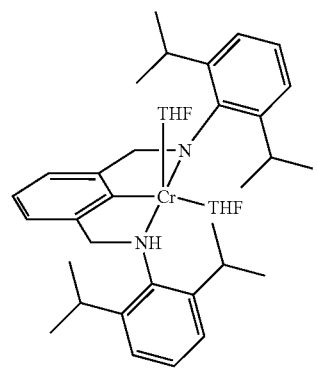

10. The method of claim 6, wherein the olefin is ethylene, propylene, or butadiene.

11. A method for isomerizing α-olefins, comprising:
    providing a NCN pincer ligand group VI metal complex according to claim 1;
    providing one or more α-olefins; and
    contacting the complex with the α-olefins, wherein the complex catalyzes the isomerization of the α-olefins to internal olefins.

12. The method of claim 11, wherein the NCN pincer ligand group VI metal complex has the structure:

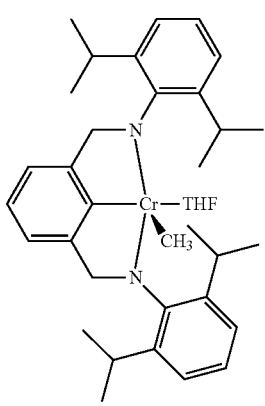

13. The method of claim 11, wherein the NCN pincer ligand group VI metal complex has the structure:
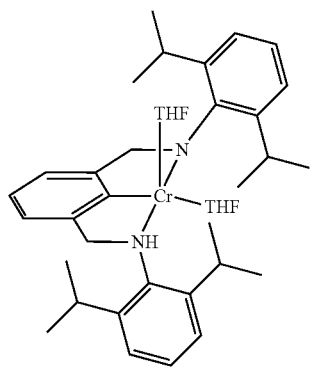
14. The method of claim 11, wherein the NCN pincer ligand group VI metal Complex has the structure:
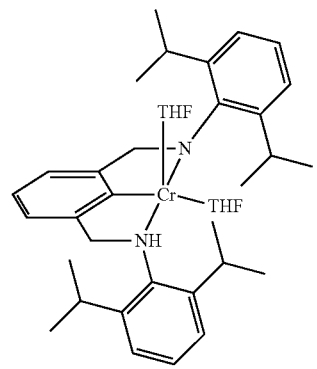
15. The method of claim 11, wherein the α-olefin is a 4 to 20 carbon having at least one vinyl group and at least one methylene unit adjacent to the vinyl group.
* * * * *

UNITED STATES PATENT AND TRADEMARK OFFICE
CERTIFICATE OF CORRECTION

PATENT NO.        : 9,637,425 B2
APPLICATION NO.   : 13/852611
DATED             : May 2, 2017
INVENTOR(S)       : Kevin P. McGowan et al.

Page 1 of 1

It is certified that error appears in the above-identified patent and that said Letters Patent is hereby corrected as shown below:

In the Specification

Column 9,
Line 31, "a-olefin to an internal olefin. The a-olefin" should read --α-olefin to an internal olefin. The α-olefin--.

Column 10,
Line 49, "the co-scan" should read --the ω-scan--.

In the Claims

Column 19,

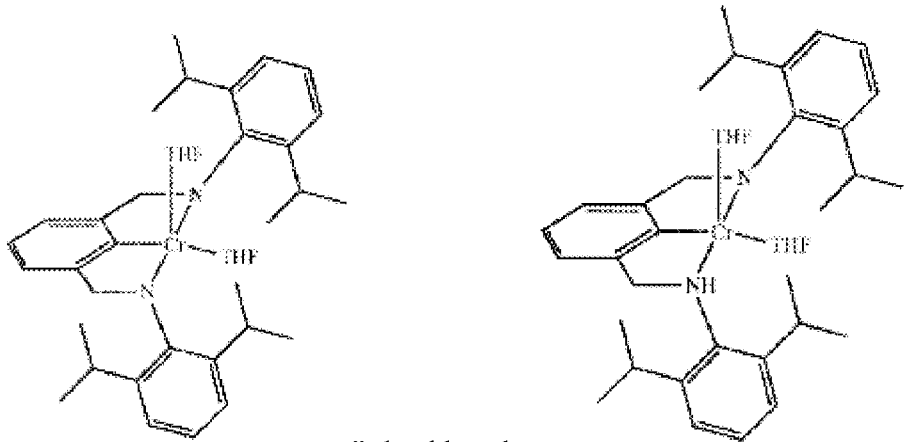

Line 42, " " should read -- --.

Column 21,
Line 21, "metal Complex" should read --metal complex--.

Signed and Sealed this
Fourteenth Day of November, 2017

Joseph Matal
*Performing the Functions and Duties of the
Under Secretary of Commerce for Intellectual Property and
Director of the United States Patent and Trademark Office*